US007645291B2

United States Patent
Ross et al.

(10) Patent No.: US 7,645,291 B2
(45) Date of Patent: *Jan. 12, 2010

(54) CUTTING BLADE ASSEMBLY FOR A MICROKERATOME

(75) Inventors: Rod Ross, Mission Viejo, CA (US);
Gregg Hughes, Mission Viejo, CA (US);
Mark Moyer, San Marcos, CA (US);
James Robert Dennewill, Cerritos, CA (US)

(73) Assignee: Med-Logics, Inc., Laguna Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/672,730

(22) Filed: Sep. 25, 2003

(65) Prior Publication Data

US 2004/0097998 A1    May 20, 2004

Related U.S. Application Data

(63) Continuation of application No. 09/585,566, filed on Jun. 2, 2000, now Pat. No. 6,663,644.

(51) Int. Cl.
*A61F 9/00* (2006.01)
(52) U.S. Cl. ........................ 606/166; 604/22
(58) Field of Classification Search ................ 606/166, 606/167, 1, 169, 171–173, 176–178, 4–5, 606/170, 132; 604/19, 22; 30/340, 342, 30/344, 346.51, 346.61, 346
See application file for complete search history.

(56) References Cited

U.S. PATENT DOCUMENTS

| 1,568,794 | A | * | 1/1926 | Baer | 30/31 |
| 2,419,114 | A | * | 4/1947 | Briegel | 606/132 |
| 2,579,029 | A | * | 12/1951 | Barker et al. | 606/132 |
| 4,690,139 | A | * | 9/1987 | Rosenberg | 606/132 |
| 5,626,594 | A | * | 5/1997 | Smith | 606/166 |
| 6,051,009 | A | * | 4/2000 | Hellenkamp et al. | 606/166 |
| 6,228,099 | B1 | * | 5/2001 | Dybbs | 606/166 |
| 6,663,644 | B1 | * | 12/2003 | Ross et al. | 606/166 |

* cited by examiner

*Primary Examiner*—Michael J Milano
*Assistant Examiner*—Victor X Nguyen
(74) *Attorney, Agent, or Firm*—The Eclipse Group LLP; David P. Gloekler

(57) ABSTRACT

A blade assembly that can be assembled into a microkeratome which is used to cut a cornea. The blade assembly is constructed in a manner that minimizes the tolerance of the cutting depth into the cornea. The blade assembly includes a blade holder that can be pressed onto a blade. The relative position of the blade holder can be calibrated to control the distance between a reference surface of the blade holder and the cutting edge of the blade. This distance defines the cutting depth of the blade. The blade holder is coupled to the blade with an interference fit that both secures the holder while providing for calibration of the assembly.

30 Claims, 5 Drawing Sheets

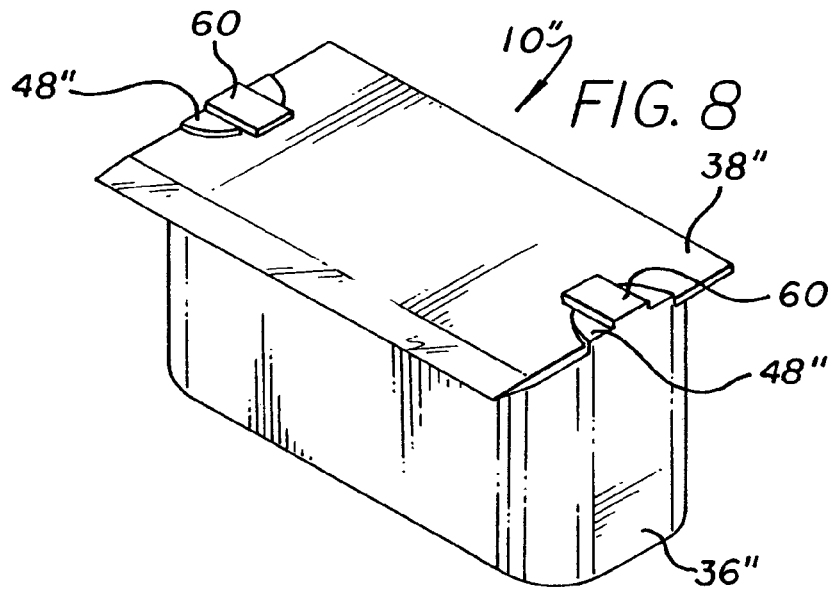
FIG. 8
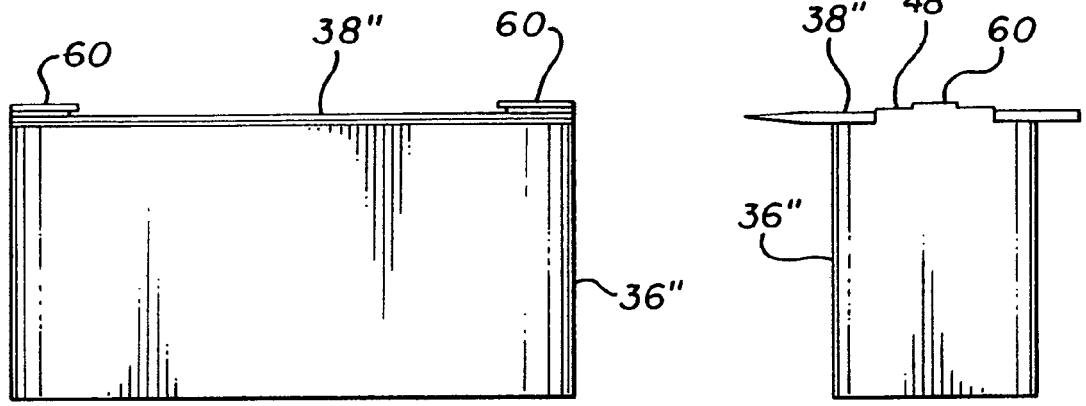
FIG. 10
FIG. 9
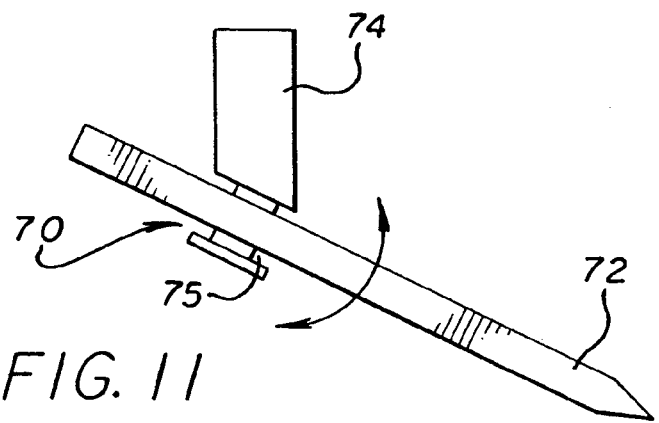
FIG. 11

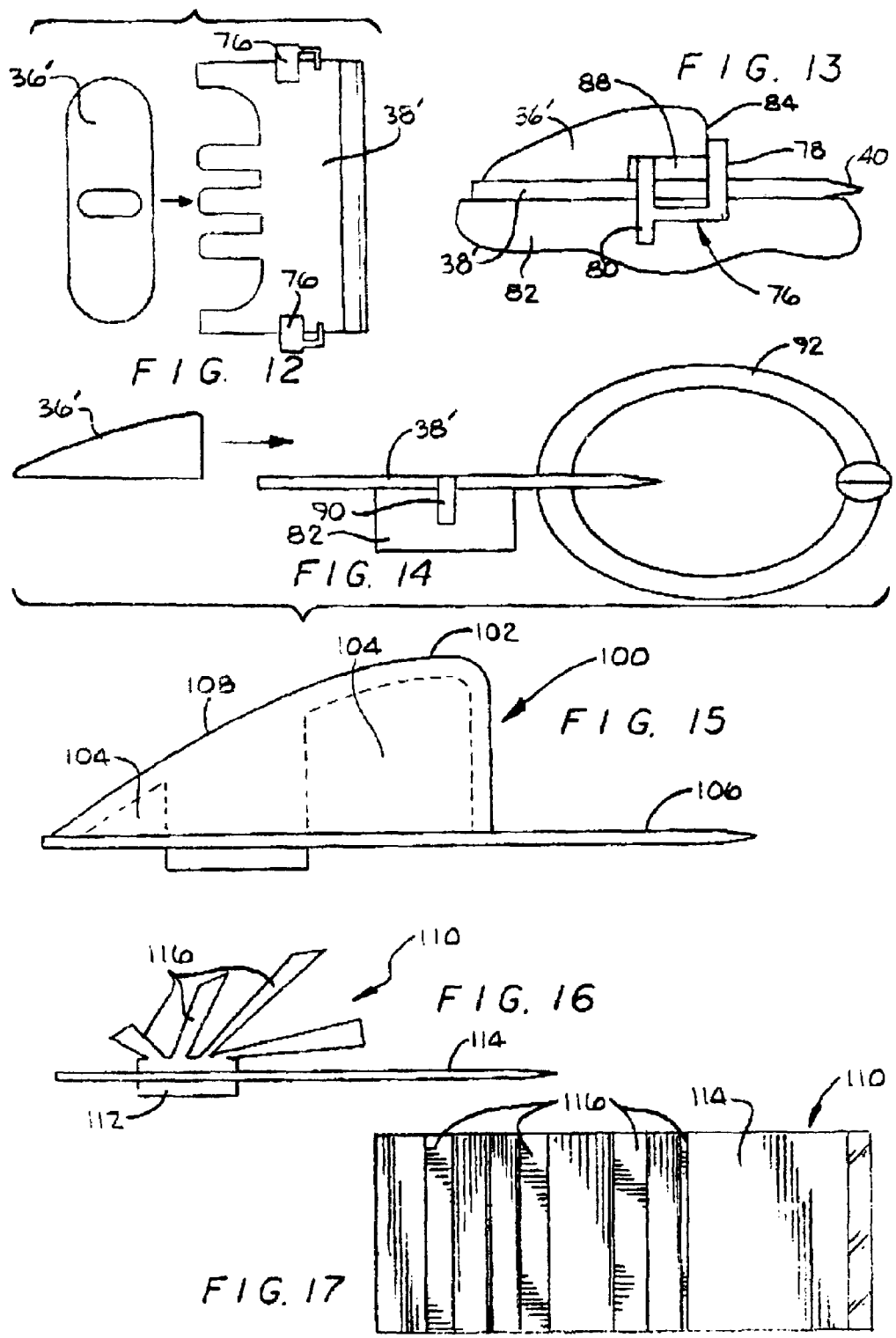

CUTTING BLADE ASSEMBLY FOR A MICROKERATOME

RELATED APPLICATIONS

This application is a continuation application of U.S. patent application Ser. No. 09/585,566, filed Jun. 2, 2000, titled "Cutting Blade Assembly for a Microkeratome," issued as U.S. Pat. No. 6,663,644 on Dec. 16, 2003; the content of which is incorporated by reference herein in its entirety.

BACKGROUND OF THE INVENTION

1. Field of the Invention

The present invention relates to a blade assembly that can be assembled into a medical device that is used to cut a cornea.

2. Prior Art

There have been developed a number of different surgical techniques to correct hyperopic or myopic conditions of a human eye. U.S. Pat. No. 4,840,175 issued to Peyman discloses a procedure wherein a thin layer of the cornea tissue is cut and removed from the cornea. A laser beam is then directed onto the exposed corneal tissue in a predetermined pattern. The laser beam ablates corneal tissue and changes the curvature of the eye. This procedure is sometimes referred to as Laser in situ Keratomileusis (LASIK).

U.S. Pat. No. Re 35,421 issued to Ruiz et al. discloses a device for cutting a cornea in a LASIK procedure. Such a device is commonly referred to as a microkeratome. The Ruiz microkeratome includes a ring that is placed onto a cornea and a blade that is located within an opening of the ring. The device also contains a drive mechanism which moves the blade across the cornea in a first direction while the blade moves in a reciprocating transverse direction to cut the eye. The device can create a lamella flap of the cornea which is flipped back so that the stromal bed of the cornea can be ablated with a laser.

U.S. Pat. No. 6,051,009 issued to Hellenkamp et al. discloses a microkeratome that is sold under the trademark HANSATOME. The HANSATOME microkeratome moves the blade in an arcuate path about the cornea. The HANSATOME includes a disposable blade assembly that can be readily loaded and removed from the device. The blade assembly includes a blade holder that is attached to a cutting blade. The blade holder has a recess that receives the end of a drive shaft. Rotation of the output shaft both moves the blade in an arcuate path and moves the blade in a back and forth motion to create the lamella flap of the cornea.

It is critical to control the depth of the cut to prevent a deep or shallow cut of the cornea. The depth of the cut is a function of the distance between the cutting edge of the blade and a reference surface of the blade holder. The HANSATOME blade holder is attached to the cutting blade by a pair of plastic protrusions that extend from the blade holder through corresponding apertures of the blade. The plastic protrusions located on the underside of the blade holder are then ultrasonically welded to the top side of the blade. The accuracy of the distance between the cutting edge and the reference surface, and thus the depth of the cut into the cornea, is dependent upon the mechanical tolerance between the cutting edge and the aperture of the blade, and the mechanical tolerance between the protrusions and the reference surface of the blade holder. This tolerance "build up" can reduce the predictability of the cutting depth. It would be desirable to provide a blade assembly and process for assembling the blade assembly that would tightly control the tolerance between the cutting edge and the reference surface and thus the depth of the cut.

BRIEF SUMMARY OF THE INVENTION

One embodiment of the present invention is a blade assembly that can be assembled to a medical device used to cut a cornea. The blade assembly may include a blade holder that is coupled to a blade. The blade has a notch.

BRIEF DESCRIPTION OF THE DRAWINGS

FIG. 8 is a perspective view of another embodiment of a blade assembly;

FIG. 9 is a side view of the blade assembly shown in FIG. 8;

FIG. 10 is front view of the blade assembly shown in FIG. 8;

FIG. 11 is a side view of another embodiment of a blade assembly;

FIG. 12 is a top view showing a blade holder and a blade secured by a stabilizing post that is used to calibrate the holder;

FIG. 13 is a side view showing the blade holder assembled to the blade;

FIG. 14 is a top view showing a blade secured by a clamp that is used to calibrate the blade holder;

FIG. 15 is a side view of another embodiment of a blade assembly;

FIG. 16 is a side view of another embodiment of a blade assembly;

FIG. 17 is a top view of the blade assembly shown in FIG. 16.

DETAILED DESCRIPTION OF THE PREFERRED EMBODIMENT

In general the present invention includes a blade assembly that can be assembled into a microkeratome which is used to cut a cornea. The blade assembly is constructed in a manner that minimizes the tolerance of the cutting depth into the cornea. The blade assembly includes a blade holder that can be pressed onto a blade. The relative position of the blade holder can be calibrated to control the distance between a reference surface of the blade holder and the cutting edge of the blade. This distance defines the cutting depth of the blade. The blade holder is coupled to the blade with an interference fit that both secures the holder while providing for calibration of the assembly.

Figure 1:
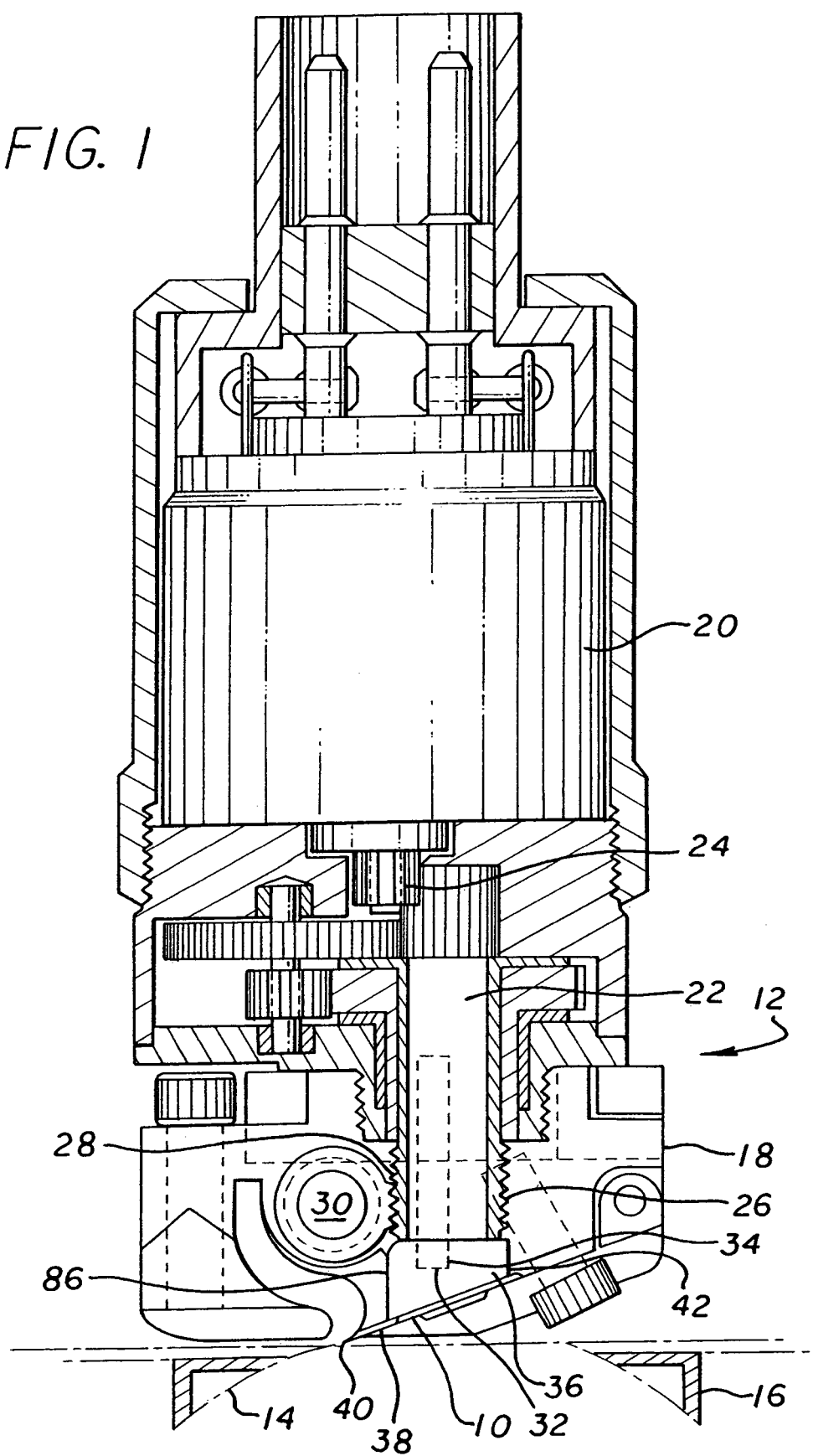
FIG. 1 is a side view of an embodiment of a microkeratome with a blade assembly of the present invention.

Referring to the drawings more particularly by reference numbers, FIG. 1 shows an embodiment of a blade assembly 10 assembled into a microkeratome 12. The microkeratome 12 is typically used to create a lamella in a cornea 14 as an initial step in a LASIK procedure. The microkeratome 12 may be the same or similar to the device disclosed in U.S. Pat. No. 6,051,009 issued to Hellenkamp et al., which is hereby incorporated by reference. The device disclosed in the '009 patent is also sold by Bausch & Lomb under the trademark HANSATOME. Although the HANSATOME is shown and described, it is to be understood that the blade assembly 10 of the present invention can be used in other microkeratomes.

The microkeratome 12 includes a ring 16 that is placed onto the cornea 14 and typically held in place by a vacuum pressure. The microkeratome 12 also includes a cutting head assembly 18 that is coupled to the ring 16. The cutting head assembly 18 includes a motor 20 that is coupled to an output shaft 22 by a gear assembly 24. The output shaft 22 has an external thread 26 that is coupled to a corresponding thread 28 of a drive shaft 30. The drive shaft 30 is coupled to a track (not shown) of the ring 16. Rotation of the output shaft 22, turns the drive shaft 30 and causes the entire cutting head assembly 18 to move about the cornea 14 along an arcuate path.

The output shaft 22 also has a pin 32 that extends into a corresponding slot 34 of a blade holder 36. The blade holder 36 is attached to a blade 38 which has a cutting edge 40 that cuts the cornea 14. Rotation of the output shaft 22 causes a reciprocating transverse movement of the blade 38. The reciprocating movement of the blade 38 cuts corneal tissue while the drive shaft 30 moves the entire assembly 18 across the cornea 14. The blade assembly 10 can be replaced by removing the assembly 10 from a blade cavity 42 of the cutting head assembly 18.

Figure 2:
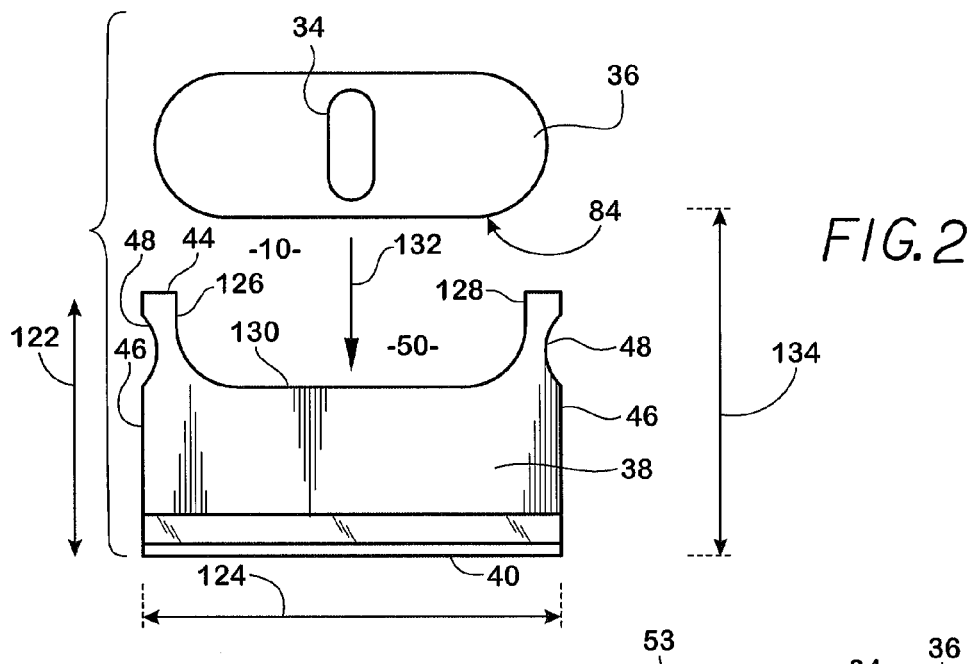
FIG. 2 is an exploded top view of an embodiment of a blade assembly.

FIG. 2 shows an embodiment of a blade assembly 10 that includes the blade holder 36 and a blade 38. The blade 38 is typically constructed from a hard stainless steel material that is stamped or machined into the configuration shown. The blade 38 is disposed in a blade plane and may include the cutting edge 40, a rear edge 44 and a pair of side edges 46. The front cutting edge 40 is disposed at a distance from the rear edge 44 along a first direction generally indicated by an arrow 122. The side edges 46 are disposed at a distance from each other along a second direction generally indicated by an arrow 124. The first direction 122 from the rear edge 44 to the front cutting edge 40 is thus a back-to-front direction and the second direction 124 is a side-to-side direction. The first direction 122 and the second direction 124 lie in the plane of the blade 38. The side edges 46 may each have a notch 48. The rear edge 44 may also have a notch 50. As illustrated in FIG. 2, the notch 50 may includes a first inside edge 126, a second inside edge 128 facing the first inside edge 126, and a third inside edge 136 interposed between the first inside edge 126 and the second inside edge 128.

The notches 48 may provide a feature that allows an operator to grab the blade assembly 10 and load the assembly 10 into the microkeratome 12. Additionally, a plurality of blades 38 may be loaded and transported on a rack (not shown) with pins that extend through the notches 48. The notches 48 may also provide reference surfaces for fixture alignment pins (not shown) used to align and calibrate the blade holder 36 with the blade 38.

Figure 3:
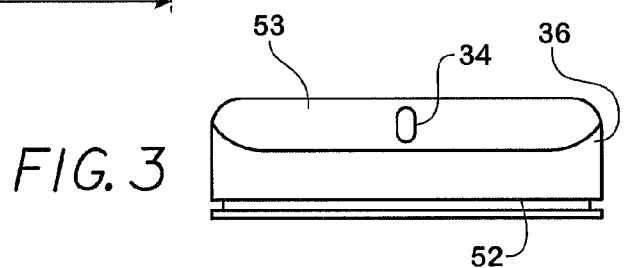
FIG. 3 is a front view of a blade holder of the blade assembly.

As shown in FIG. 3, the blade holder 36 may have an outer groove 52. The blade holder 36 may also have a tapered top surface 53 to provide clearance for the pin 32 when the blade assembly 10 is loaded into the microkeratome 12. The blade holder 36 may be constructed from a plastic material, wherein the groove 52 and slot 34 are either molded or machined into the blade holder 36. Referring to FIG. 2, the blade holder 36 can be assembled onto the blade 38 by pushing the blade holder 36 into the notch 50 as indicated by an arrow 132, so that the edge of the notch 50 extends into the groove 52 (FIG. 3) of the side of the blade holder 36. The front side of the blade holder 36 generally facing the front cutting edge 40 includes a reference surface 84 (see also FIG. 13) that may generally adjoin the top surface 53 (FIG. 3). When the blade assembly 10 is installed in the blade cavity 42 of a cutting head assembly 18 such as illustrated by example in FIG. 1, the reference surface 84 of the blade holder 36 abuts against a corresponding reference surface 86 of the cutting head assembly 18 (such as may be located in or provided as an inside surface of the blade assembly cavity 42 shown in FIG. 1). As noted previously, the distance between the reference surface 84 of the blade holder 36 and the front cutting edge 40 of the blade 38 dictates the cutting depth of the blade 38. In FIG. 2, this distance is indicated by an arrow 134. It can be seen that this distance 134 may be adjusted, and the cutting depth thereby controlled or selected, during the assembly of the blade assembly 10. That is, in the present example the distance 134 may be adjusted by how far the blade holder 36 is pushed into the notch 50 of the blade 38 along the direction 132 (or, similarly, along the above-referenced first direction 122, or in the back-to-front direction).

Figure 4:
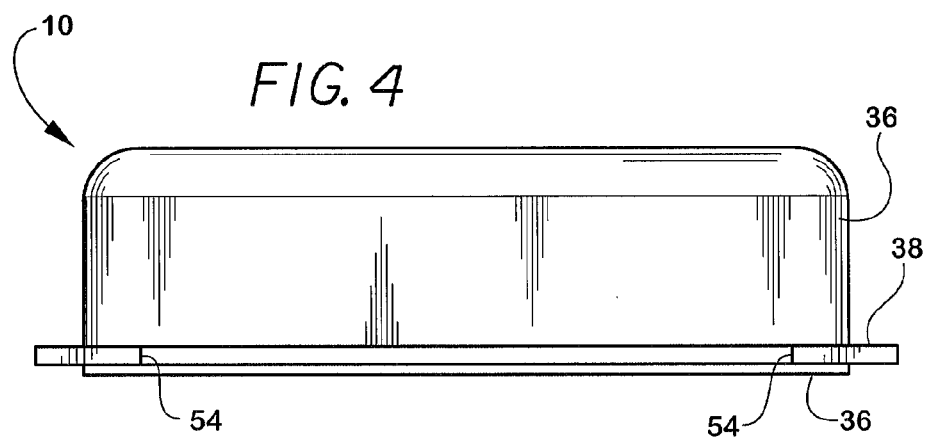
FIG. 4 is a side view of the blade assembly.

As shown in FIG. 4, the blade holder 36 engages the inner edges 54 of the blade notch 50. The blade holder 36 is held in place by frictional forces between the blade holder 36 and the edges 54 to create a frictional fit. The blade holder 36 may be further secured to the blade 38 by an adhesive or other means.

Figure 5:
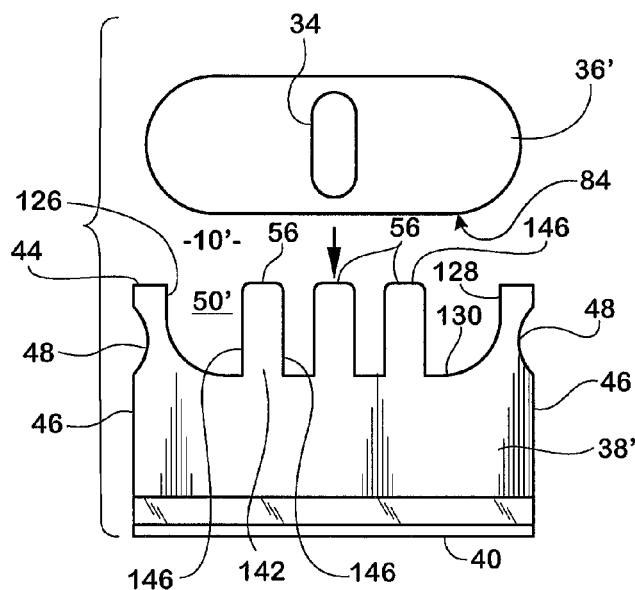
FIG. 5 is an exploded top view of another embodiment of a blade assembly.
Figure 6:
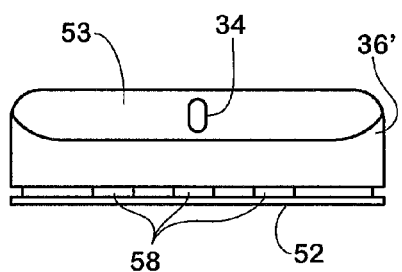
FIG. 6 is a side view of a blade holder of the assembly shown in FIG. 5.
Figure 7:
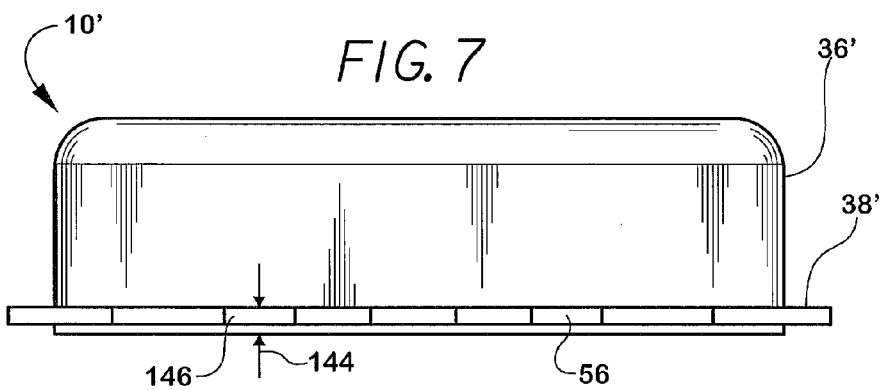
FIG. 7 is a side view of the blade assembly shown in FIG. 5.

FIGS. 5, 6 and 7 show another embodiment of a blade assembly 10'. In this embodiment, the blade 38' has a plurality of fingers 56 within the notch 50'. The fingers 56 may extend in a direction opposite and away from the cutting edge 40 of the blade 38', in a generally coplanar relation with the blade 38'. The fingers 56 can extend into corresponding slots 58 of the blade holder 36'. The fingers 56 increase the surface area and corresponding frictional forces that couple the blade 38' to the blade holder 36. As illustrated, each finger 56 includes an area 142 (FIG. 5), a thickness 144 (FIG. 7) perpendicular to the area 142, and a finger edge 146 (FIGS. 5 and 7) bounding the area 142 and extending along the direction of the thickness 144. One or more portions of the finger edge 146 may frictionally engage the corresponding slot 58 of the blade holder 36'. As in the case of the implementation described above and illustrated in FIGS. 2-4, the distance between the reference surface 84 of the blade holder 36' and the front cutting edge 40 of the blade 38' is adjustable by the amount by which the blade holder 36' is pushed into the notch 50' of the blade 38', and in the present example by how far the fingers 56 extend into the slots 58.

FIGS. 8, 9 and 10 show yet another embodiment of a blade assembly 10". The blade holder 36" of the assembly 10" has a pair of clips 60 that secure the holder 36" to the blade 38" within blade notches 48". The clips 60 secure the holder 36" to the blade 38" with frictional forces. With this embodiment the blade holder 36" can move relative to the blade 38" during installation into the microkeratome 12. The relative movement provides a mechanical float feature that compensates for tolerances in the cutting head assembly 18, particularly the cavity 42 of the microkeratome.

FIG. 11 shows another embodiment of a blade holder assembly 70 wherein a blade 72 can pivot relative to the blade holder 74 as indicated by the arrow. This embodiment provides a mechanical float that will compensate for tolerances in the assembly 20 and the microkeratome 12. The float is created by a gap 75 between the blade holder 74 and the blade 72. The blade holder 74 may be held in place by frictional forces between an inner edge of the holder 74 and an outer edge of the blade 72.

FIGS. 12 and 13 show a method for assembling and calibrating the blade holder 36' to the blade 38'. The blade 38' may be held in place by a pair of stabilizer posts 76. The posts 76 extend through the notches 48 (FIG. 2) of the blade 38'. Each stabilizer post 76 includes a stop 78 that is connected to a pin 80. Each pin 80 is attached to a fixture plate 82.

The blade holder 36' is pushed onto the blade 38' until a reference surface 84 of the blade holder 36' abuts against the stop 78. The reference surface 84 rests against a corresponding reference surface 86 of the cutting head assembly 18 shown in FIG. 1. The stop 78 provides a datum point that closely controls the distance between the reference surface 84 and the cutting edge 40 of the blade 38. The distance between the reference surface 84 and the cutting edge 40 defines the cutting depth of the blade 38'. The blade holder 36' may have a pair of outer notches 88 that provide a clearance for the pins 80 when the holder 36' is pushed onto the blade '38.

FIG. 14 shows another means for assembling and calibrating the blade holder 36' to the blade 38'. The blade 38' can be secured to a fixture plate 82 by a couple of pins 90 that extend into the blade notches. A clamp 92 is then coupled to the blade 38. The blade holder 36' is pushed onto the blade 38' until the reference surface 84 abuts against the clamp 92. The distance between the clamp 92 and the cutting edge 40 can be accurately controlled to minimize the tolerance between the reference surface 84 and the cutting edge 40.

FIG. 15 shows another embodiment of a blade assembly 100 that includes a blade holder 102 which has one or more cavities 104. The blade holder 102 is coupled to a blade 106 by any of the embodiments shown in FIGS. 2-11. The cavities 104 reduce the stiffness of the blade holder 104 so that the blade holder 102 can be more readily installed into an undersized blade cavity 42. Additionally, a tool (not shown) can be inserted in a cavity 104 and used to push the blade holder 102 onto the blade 106. The blade holder 102 may also have a contoured top surface 108 that reduces the surface area in contact with the cutting head assembly 18. The contoured surface 108 reduces the tolerance requirements of the holder 102 and the cavity 42.

FIGS. 16 and 17 show another embodiment of a blade assembly 110 that includes a blade holder 112 coupled to a blade 114. The blade holder 112 can be attached to the blade 114 by an interference fit as described in FIGS. 2-11. The blade holder 112 includes a plurality of fingers 116. The fingers 116 provide a means to grasp the assembly 110. The individual fingers 116 also minimize the friction and lack of fit with the blade cavity 42. The most distal finger 116 provides a reference surface that abuts against the corresponding reference surface of the cavity 42.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

For example, although the blade assembly 10 shown in FIG. 2 shows a notch 50 in the blade 38, the assembly 10 could be constructed to eliminate the notch 50 and form a deep groove within the blade holder 36', essentially a mirror image of the embodiment shown.

What is claimed is:

1. A blade assembly that can be loaded into an inner cavity of a microkeratome, the blade assembly comprising:
   a blade disposed in a blade plane, the blade including a front cutting edge, a rear edge opposite the front cutting edge and disposed at a distance from the front cutting edge along a first direction, a first side edge, and a second side edge disposed at a distance from the first side edge along a second direction, the first direction and the second direction lying in the blade plane; and
   a blade holder including a blade holder reference surface generally facing toward the front cutting edge, and an opening configured to receive a pin of the microkeratome, the blade holder frictionally engaging the rear edge and movable relative to the rear edge toward the front cutting edge by an amount adjustable along the first direction, wherein the blade holder reference surface is positioned at an adjustable distance from the front cutting edge along the first direction.

2. The blade assembly of claim 1, wherein said blade holder has a clip that is attached to said blade.

3. The blade assembly of claim 1, wherein said blade can pivot relative to said blade holder.

4. The blade assembly of claim 1, wherein said blade holder has a cavity.

5. The blade assembly of claim 1, wherein said blade holder has an outer groove.

6. The blade assembly of claim 1, wherein the rear edge includes a notch and the blade holder engages the notch.

7. The blade assembly of claim 6, wherein the notch includes a first inside edge, a second inside edge facing the first inside edge, and a third inside edge interposed between the first inside edge and the second inside edge, and the blade holder frictionally engages the first inside edge and the second inside edge.

8. The blade assembly of claim 6, wherein the blade holder has an outer groove and the outer groove engages the notch.

9. The blade assembly of claim 8, wherein the blade includes a finger extending outwardly from the notch in a direction away from the front cutting edge, the blade holder includes a slot extending from the outer groove, and the finger extends into the slot.

10. The blade assembly of claim 1, wherein the blade holder has an outer groove and the outer groove engages the rear edge.

11. The blade assembly of claim 10, wherein the blade includes a finger extending outwardly from the rear edge in a direction away from the front cutting edge, the blade holder includes a slot extending from the outer groove, and the finger extends into the slot.

12. The blade assembly of claim 1, wherein the blade includes a finger extending outwardly from the rear edge in a direction away from the front cutting edge, the blade holder includes a slot, and the finger extends into the slot.

13. The blade assembly of claim 1, wherein the blade includes a plurality of fingers extending outwardly from the rear edge in a direction away from the front cutting edge, the blade holder includes a plurality of slots, and the fingers extend respectively into the slots.

14. The blade assembly of claim 1, wherein the first side edge includes a first notch and the second side edge includes a second notch.

15. The blade assembly of claim 1, wherein the blade holder includes a tapered top surface and the opening is formed in the tapered top surface.

16. A blade assembly that can be loaded into an inner cavity of a microkeratome, the inner cavity including an inner cavity reference surface, the blade assembly comprising:
   a blade disposed in a blade plane, the blade including a front cutting edge, a rear edge opposing the front cutting edge and disposed at a distance from the front cutting edge along a first direction, a first side edge, and a second side edge disposed at a distance from the first side edge along a second direction, the first direction and the second direction lying in the blade plane; and a blade holder including a front side generally facing toward the front cutting edge and an opening configured to receive a pin of the microkeratome, the front side including a blade holder reference surface, the blade holder being pressed into frictional engagement with the rear edge by an amount adjustable along the first direction toward the front cutting edge, wherein the blade holder reference surface is positioned at an adjustable distance from the cutting edge along the first direction, and the blade holder reference surface is configured to contact the inner cavity reference surface when the blade assembly is loaded in the inner cavity.

17. The blade assembly of claim 16, wherein the rear edge includes a notch and the front side engages the notch.

18. The blade assembly of claim 17, wherein the notch includes a first inside edge, a second inside edge facing the first inside edge, and a third inside edge interposed between the first inside edge and the second inside edge, and the blade holder frictionally engages the first inside edge and the second inside edge.

19. The blade assembly of claim 16, wherein the blade includes a finger extending outwardly from the rear edge in a direction away from the front cutting edge, the blade holder includes a slot, and the finger extends into the slot.

20. The blade assembly of claim 16, wherein the blade includes a plurality of fingers extending outwardly from the rear edge in a direction opposite and away from the front cutting edge, the blade holder includes a plurality of slots, and the fingers extend respectively into the slots.

21. A blade assembly that can be loaded into an inner cavity of a microkeratome, the blade assembly comprising:

a blade disposed in a blade plane, the blade including a front cutting edge, a rear edge opposing the front cutting edge, a first side edge, a second side edge opposing the first side edge, and a finger extending outwardly from the rear edge in a direction opposite and away from the front cutting edge and generally coplanar with the blade plane; and a blade holder including a slot, and an opening configured to receive a pin of the microkeratome, wherein the blade holder contacts the rear edge and the finger extends into the slot along the blade plane.

22. The blade assembly of claim 21, wherein the rear edge includes a notch, the blade holder contacts the notch, and the finger extends from the notch.

23. The blade assembly of claim 21, wherein the finger frictionally engages the slot.

24. The blade assembly of claim 21, wherein the finger has an area, a thickness perpendicular to the area, and a finger edge extending along the direction of the thickness, and the finger edge frictionally engages the slot.

25. The blade assembly of claim 21, wherein the finger is one of a plurality of fingers extending outwardly from the rear edge in a direction opposite and away from the front cutting edge, the slot is one of a plurality of slots of the blade holder, and the fingers extend respectively into the slots.

26. The blade assembly of claim 21, wherein the blade holder frictionally engages the blade.

27. The blade assembly of claim 21, wherein the rear edge is disposed at a distance from the front cutting edge along a first direction, the second side edge is disposed at a distance from the first side edge along a second direction, the blade holder includes a blade holder reference surface generally facing toward the front cutting edge, the blade holder is movably engaged with the blade by an amount adjustable along the first direction toward the front cutting edge, and the blade holder reference surface is positioned at an adjustable distance from the front cutting edge along the first direction.

28. The blade assembly of claim 21, wherein the first side edge includes a first notch and the second side edge includes a second notch.

29. The blade assembly of claim 21, wherein the blade holder includes a tapered top surface and the opening is formed in the tapered top surface.

30. The blade assembly of claim 21, wherein said blade holder has a cavity.

* * * * *